US00PP26712P3

(12) United States Plant Patent
Nir

(10) Patent No.: US PP26,712 P3
(45) Date of Patent: May 10, 2016

(54) ***ADENANTHOS* PLANT NAMED 'CHRISTAL'**

(50) Latin Name: *Adenanthos sericeus*
Varietal Denomination: CHRISTAL

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 101 days.

(21) Appl. No.: 13/999,888

(22) Filed: Mar. 31, 2014

(65) Prior Publication Data

US 2015/0282413 P1 Oct. 1, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV—PLUTO Plant Variety Database, Jul. 22, 2015, citation for 'Tal'.*

* cited by examiner

*Primary Examiner* — Susan McCormick Ewoldt
(74) *Attorney, Agent, or Firm* — Cassandra Bright

(57) ABSTRACT

A new and distinct *Adenanthos* cultivar named 'CHRISTAL' is disclosed, characterized by unique branch structure. The new variety is a *Adenanthos*, normally used for ornamental foliage, or landscape purposes.

1 Drawing Sheet

Latin name of the genus and species: *Adenanthos sericeus*.
Variety denomination: 'CHRISTAL'.

BACKGROUND OF THE INVENTION

The new *Adenanthos* cultivar is a product of open pollination. The new variety was discovered as a seedling growing in a field of various *Adenanthos sericeus* varieties by the inventor, Nitzan Nir, in Kfar Hess, Israel. The new variety was selected during 2008, at a commercial nursery in Kfar Hess, Israel. The exact parents are unknown, and believed to be unnamed varieties of *Adenanthos*.

Asexual reproduction of the new cultivar has been performed by vegetative cuttings. This was first performed at a commercial nursery in Kfar Hess, Israel in 2008 and has shown that the unique features of this cultivar are stable and reproduced true to type in 6 successive generations.

SUMMARY OF THE INVENTION

The cultivar 'CHRISTAL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHRISTAL'. These characteristics in combination distinguish 'CHRISTAL' as a new and distinct *Adenanthos* cultivar:

1. Unique branch structure forming a triangular, Christmas tree shaped plant.

PARENT COMPARISON

The parents are unknown to the inventor.

COMMERCIAL COMPARISON

Plants of the new cultivar 'CHRISTAL' are compared to the unnamed, unpatented commercial variety *Adenanthos sericeus*. Varieties are similar in most horticultural characteristics; however 'AVIV' differs in the following characteristics;

1. Different branch structure.

Plants of the new cultivar 'CHRISTAL' can also be compared to the commercial variety Adenanthos 'NIR AVIV'; having Ser. No. 13/999,886. The varieties are similar in most horticultural characteristics; however 'CHRISTAL' differs in the following characteristics;

1. Different branch structure
2. Upright plant habit, compared to prostrate plant habit.

BRIEF DESCRIPTION OF THE PHOTOGRAPH

The accompanying photograph in FIG. 1 illustrates in full color a typical plant of 'CHRISTAL' grown in a commercial greenhouse in Kfar, Israel. The plant is 4-5 months old from a rooted cutting, in a 15 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe typical plant of 'CHRISTAL' grown in a commercial greenhouse in Kfar, Israel. The plant is at least 2 months old from a rooted cutting, in a 25 cm pot. The growing temperature ranged from 15° C. to 35° C. during the day and from −2° C. to 35° C. during the night. General light conditions are bright, normal sunlight. Measurements and numerical values represent averages of typical plant types. Chemical treatments included general fungicides and insecticides.

Botanical classification: *Adenanthos sericeus* 'CHRISTAL'.

PROPAGATION

Time to produce a rooted plantlet: 30 to 60 days at approximately 24° C.
Root description: Semi-woody, fine.

PLANT

Growth habit: Upright evergreen shrub, forming a triangular shaped plant.
Height: 300-500 cm to top of foliage.
Plant spread: 200 cm.
Branching characteristics:
Length of primary lateral branches: 60 cm on 4 to 5 month plant.
Quantity of primary lateral branches: 120.
Characteristics of primary lateral branches:
*Form*.—Round.
*Diameter*.—0.4-0.6 cm.
*Color*.—Greyed-green 194A RHS.
*Texture*.—Hairy.
*Strength*.—Flexible.
Internode length: 0.5-7.0 cm. (measured in section of 20 cm from top).

FOLIAGE

Leaf:
*Arrangement*.—Alternate.
*Quantity*.—Approximately 9 leaves, in the 10-15 cm section from the top of the branch.
*Average length*.—3.7 cm.
*Average width*.—2.0 cm.
*Shape of blade*.—Needle.
*Apex*.—Needle-shaped.
*Base*.—Elliptical.
*Margin*.—Round.
*Texture of surface*.—Hairy.
*Aspect*.—Straight.
*Color*.—Young foliage upper side: Yellow-green 146C RHS. Young foliage under side: Yellow-green 146C RHS. Mature foliage upper side: Green 137A RHS. Mature foliage under side: Green 137A RHS.
*Venation*.—Indistinguishable.
*Petiole*.—Length: 0.6 cm. Diameter: 0.1 cm. Color: Green 137A RHS. Texture: Hairy.

FLOWER

Natural flowering season: Flowering rare in *Adenanthos* and not observed to date with new variety.

OTHER CHARACTERISTICS

Disease/pest resistance: Neither resistance nor susceptibility to the normal diseases and pests of *Adenanthos* have been observed to date.
Temperature tolerance: From −2° C. to 35° C.
Drought tolerance: Extremely drought tolerant.

What is claimed is:

1. A new and distinct cultivar of *Adenanthos* plant named 'CHRISTAL' as herein illustrated and described.

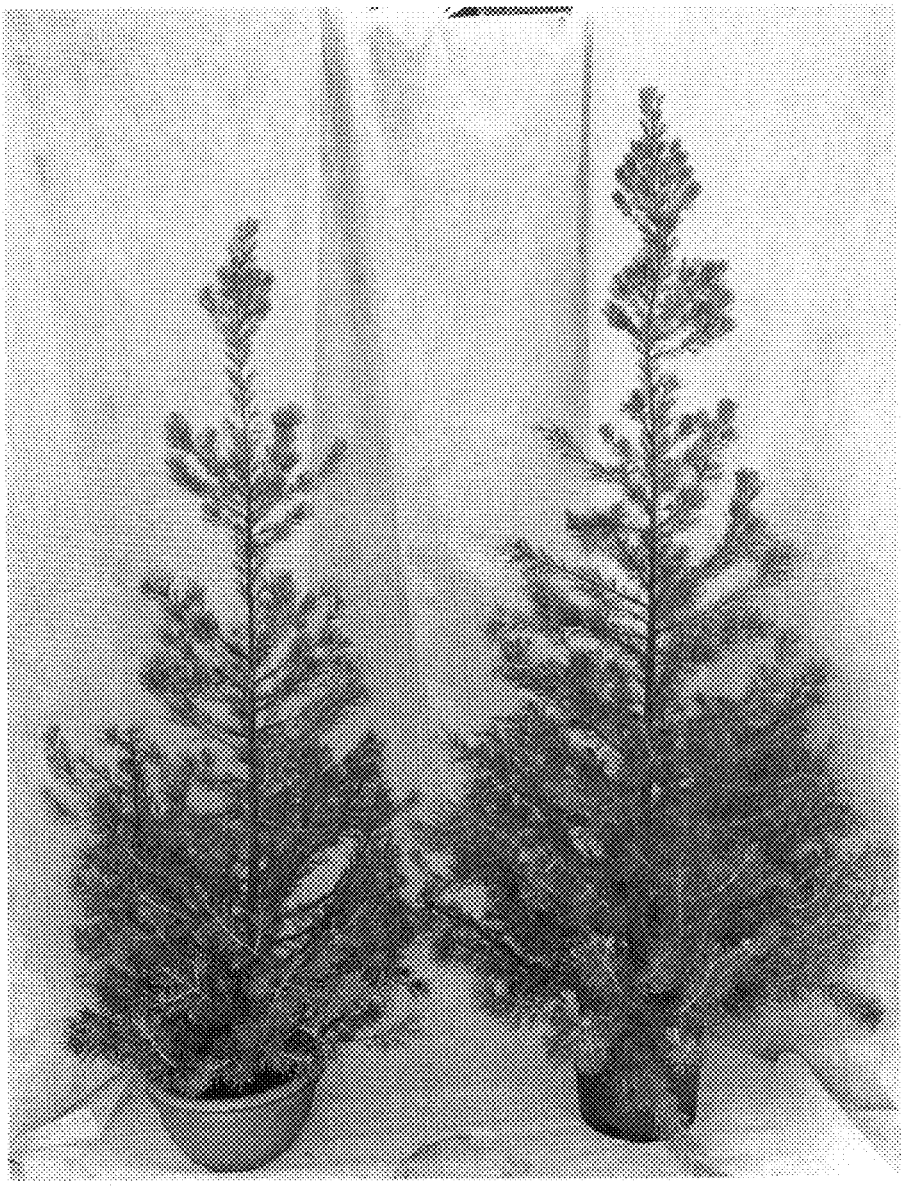

* * * * *